United States Patent [19]
Abel et al.

[11] Patent Number: 5,135,848
[45] Date of Patent: Aug. 4, 1992

[54] METHODS FOR EVALUATING CHOLESTEROL METABOLISM AND REAGENTS THEREFOR

[75] Inventors: John H. Abel, Bethlehem; Barbara Obrepalska-Bielska, Allentown, both of Pa.

[73] Assignee: Lehigh University and Northeast Benjamin Franklin Technology Center of PA, Bethlehem, Pa.

[21] Appl. No.: 425,552

[22] Filed: Oct. 23, 1989

[51] Int. Cl.$^5$ .......................................... G01N 33/567
[52] U.S. Cl. .................. 435/7.21; 435/7.24; 435/962; 435/968; 436/71; 436/503; 436/811; 530/359
[58] Field of Search .................. 435/7.2, 7.24; 436/71, 436/503, 811; 530/359, 830

[56] References Cited
PUBLICATIONS

L. S. Barak and W. W. Webb (1981) *J. Cell Biol.* 90:595–604.
D. L. Ebert et al. (1988) *J. Lipid Res.* 29:1501–1509.
J. A. Cuthbert and P. E. Lipsky (1989) *Arteriosclerosis Suppl.* I 9:I-43-I-49.
K. Suzuki et al. (1990) *Biochim. Biophys. Acta* 1042:352–358.
K. May et al. (1990) *J. Lipid Res.* 31:1683–1691.
K. N. Traill et al., (1987) *Mech. Ageing Dev.* (IRELAND) 40(3):261–288.
I. Melzner et al. (1983) *Acta Histochem. Suppl.* (Jena) 28:199–207.
T. T. Chen and J. H. Abel, Jr. (1986) *Eur. J. Cell. Biol.* 39:(2):410–416.
Huettinger et al. (1984) *J. Clin. Invest.* 74(3):1017–1026.
A. P. Wojciechowski et al. (1987) *Biochem. Soc. Trans* 15(2):251–252.
M. J. Rudling and C. O. Peterson (1985) *Biochim. Biophys. Acta* 833(3):359–365.
Y. K. Ho et al., *J. Exp. Med.*, 145:1531–1549 (1977).
Y. K. Ho et al., *J. Clin. Invest.*, 58:1465–1474 (1976).
C. F. Semenkovich and R. E. Ostlund, *J. Clin. Endocrin. and Metab.*, 62(6):1279–1287 (1986).
M. S. Brown and J. L. Goldstein, *Science*, 191:150–154 (1976).
J. S. Goldstein and M. S. Brown, *Ann. Rev. Biochem.*, 46:897–930 (1977).
M. S. Brown and J. L. Goldstein, *Science*:232:34–47 (1986).
P. T. Kovanen et al., *Proc. Nat'l Acad. Sci. USA*, 78(2):1194–1198 (1981).
Bachorik et al., *Biochemistry* 21:5675–5684, 1982.
Anderson et al., *Meth. Enzymol.* 129:201–216, 1986.
Patsch et al., *Meth. Enzymol.* 129:3–26, 1986.
Innerarity et al., *Meth. Enzymol.* 129:542–565, 1986.
Gavigan et al., *Eur. J. Biochem* 171:355–361, 1988.
Beisiegel et al., *J. Biol. Chem.* 256:11923–11931, 1988.

*Primary Examiner*—Esther L. Kepplinger
*Assistant Examiner*—Donna C. Wortman
*Attorney, Agent, or Firm*—Hamilton, Brook, Smith & Reynolds

[57] ABSTRACT

Two diagnostic methods for evaluating LDL mechanism in a patient are disclosed. A novel diagnostic agent for evaluating LDL metabolism comprising a ligand capable of binding LDL receptors and a fluorescent label and a diagnostic kit for evaluating LDL metabolism which utilized the specified diagnostic agent are also disclosed.

34 Claims, 1 Drawing Sheet

METHODS FOR EVALUATING CHOLESTEROL METABOLISM AND REAGENTS THEREFOR

BACKGROUND OF THE INVENTION

1. Field of the Invention

The present invention relates to the cardiovascular medical field and more particularly to methods for evaluating cholesterol (lipoprotein) metabolism and screening patients who have a genetic predisposition for atherosclerosis.

2. Background of the Invention

Atherosclerosis is the underlying cause of the majority of cardiovascular disease related deaths in the Western Hemisphere. The clinical effects of atherosclerosis result from the formation of plaque and blood clots within the lining of blood vessels which lead to arterial stenosis. Atherosclerosis at its worst has debilitating effects on blood flow to critical organs of the body and is the major cause of heart attacks and strokes in patients. Attempts to alleviate or reduce the etiology of atherosclerosis have been met with only modest clinical success.

While several risk factors have been linked to the disease, studies have shown that an elevated serum cholesterol level is one of the main causes of atherosclerotic plaque formation. Cholesterol itself does not exist in a free-form in the circulation, but rather in macromolecular forms of low density lipoproteins (LDL) and high density lipoproteins (HDL). Modified (oxidized or acetylated) LDL is the harmful moiety of cholesterol. Plaque formation results when the homeostasis of lipid metabolism is unbalanced leading to an excess of modified LDL. Recently, it has been found that hypercholesterolemia (elevated blood cholesterol levels) is not solely related to dietary intake of cholesterol. Regulation of serum cholesterol levels is controlled by three variables: dietary intake, endogenous production, and cellular metabolism.

Of these three, cellular metabolism is the most important variable in regulating serum cholesterol levels. This inducible system is regulated in most individuals with elevated serum cholesterol levels. It is believed that the clinical management of certain patients having elevated cholesterol levels would be improved if their cellular metabolism for cholesterol could be evaluated in a comprehensive manner. Thus, a need exists for diagnostic methods for evaluating cholesterol metabolism in patients.

SUMMARY OF THE INVENTION

It has been found that cholesterol metabolism can be evaluated by monitoring the interactions of low density lipoproteins (LDL) with receptors on blood derived cells from a patient. The present invention provides two diagnostic methods for evaluating LDL metabolism in a patient. The invention further provides a novel diagnostic agent for evaluating LDL metabolism comprising a ligand capable of binding LDL receptors and a fluorescent label and a diagnostic kit for evaluating LDL metabolism which utilizes the specified diagnostic agent.

The first diagnostic method for evaluating LDL metabolism in a patient comprises the steps of (a) contacting blood derived cells from the patient with a labeled ligand capable of binding LDL receptors; (b) incubating the resulting mixture from step (a) under conditions which allow cellular binding of the ligand and inhibit cellular internalization of the ligand; and (c) evaluating cellular binding of the labeled ligand.

The second diagnostic method for evaluating LDL metabolism in a patient comprises the steps of (a) contacting blood derived cells from the patient with a labeled ligand capable of binding LDL receptors; (b) incubating the resulting mixture from step (a) under physiological conditions for a period sufficient to allow cellular internalization of the ligand-receptor complex; and (c) evaluating cellular internalization of the labeled ligand. In one embodiment, the blood derived cells are incubated in a cholesterol-free medium prior to step (a) to derepress (upregulate) expression of LDL receptors on the blood derived cells.

DETAILED DESCRIPTION OF THE INVENTION

Figure 1:
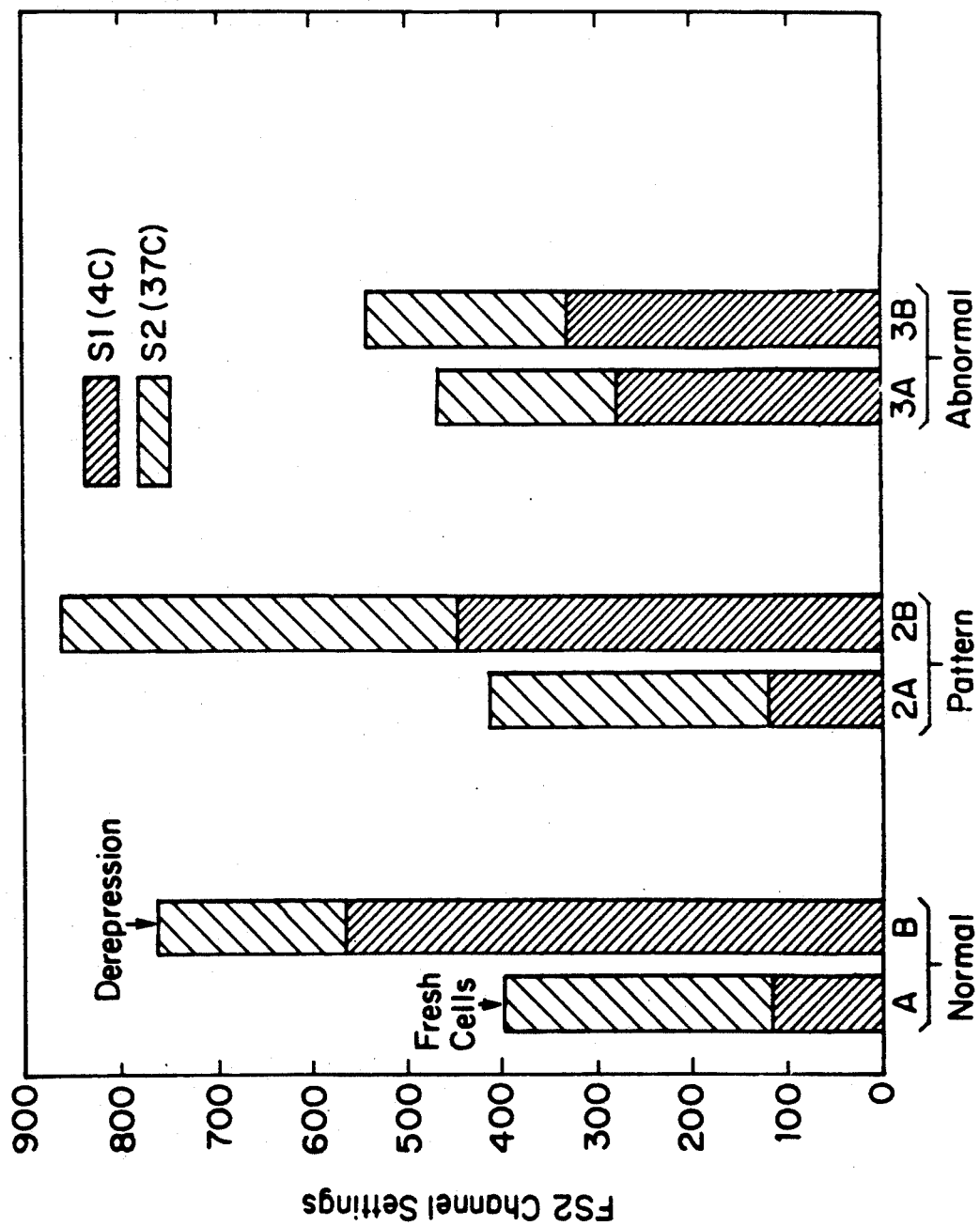
FIG. 1 shows the results of binding labeled LDL to white blood cells (WBCs) in two normal (1,2) and one abnormal (3) patient. Bar graph 1A and 2A indicate that the amount of total LDL uptake (37°) is approximately three times the binding ability at 4° C. Bar graph 1B and 2B indicate a 400% increase in receptor number resulting from receptor upregulation following incubation in lipid-free medium. Bar graph 3A indicates that, although receptor number appears increased in the abnormal patient, uptake is proportionately less. Bar graph 3B shows little significant upregulation of receptor number.

The present invention provides diagnostic methods for monitoring cholesterol metabolism and screening for individuals who have an elevated risk of developing atherosclerosis. The methods monitor the number of LDL receptors on blood derived cells, specifically white blood cells, the rate of LDL and receptor internalization, and the rate of synthesis of LDL receptors. In preferred embodiments, the present methods for evaluation of LDL metabolism employ a novel diagnostic agent comprising a ligand capable of binding LDL receptors and a fluorescent label.

In the first method of the invention, blood derived cells from a patient are contacted with a labeled ligand capable of binding LDL receptors and the resulting mixture is incubated under conditions which allow cellular binding of the ligand and inhibit cellular internalization of the ligand. Suitable sources of the blood derived cells include EDTA (ethylenediamine tetraacetic acid) or heparin anti-coagulated whole blood and WBCs isolated from whole blood in accordance with conventional technique. The preferred source of blood derived cells is ACD (sodium citrate, citric acid, dextrose) anti-coagulated whole blood and the most preferred source is CPD (citrate, phosphate, dextrose) anti-coagulated whole blood. Preferably, the blood derived cells have a white blood cell concentration of from about $5 \times 10^5$ WBCs/mL to about $4 \times 10^6$ WBCs/mL and, most preferably, a concentration of from about $1 \times 10^6$ WBCs/mL to about $5 \times 10^6$ WBCs/mL.

Suitable labeled ligands are capable of binding LDL receptors and include LDL purified from a biological source and antibodies (or fragments thereof) specific for LDL receptors. Preferably, LDL is purified from whole blood of human, bovine, canine, avian, equine or porcine origin and, most preferably, from human or porcine origin. Suitable labels for the ligand include fluorescent lipid dyes, and radiolabels. Preferably, labeled antibodies are employed at a concentration of about 10 ug protein/mL to about 40 ug protein/mL and labeled LDL is employed at a concentration of about 0.5 ug protein/mL to about 200 ug protein/mL. Most preferably, labeled LDL is employed at a concentration of from about 10 ug protein/mL to about 20 ug protein/mL.

Suitable buffers employed during the incubation for binding labeled ligand to the LDL receptors include most organic and ionic buffers or phosphate buffered saline (PBS) having a pH of from about 7.2 to about 8.0 and preferably from about 7.4 to about 7.5. Preferred buffers are phosphate, bicarbonate, HEPES (N-2-hydroxyethylpiperazine-N'-2-ethanesulfonic acid), and Tris (hydroxymethylaminome and the most preferred buffer is Hank's balanced salt solution (HBSS) supplemented with 2 mg bovine serum albumin/mL and 2 mM calcium at pH 7.4. Preferably, the buffer is supplemented with calcium in an amount of from about 1 mM to about 3 mM and bovine serum albumin (BSA) in an amount of from about 1 mg/mL to about 5 mg/mL.

Preferably, the incubation is conducted for a period of from about 30 minutes to about 20 hours and, most preferably, for a period of about 2 hours. Suitable temperatures for the incubation are from about 1° C. to about 15° C. and, preferably, from about 1° C. to about 4° C. Following incubation, cellular binding of the labeled ligand-receptor composition is evaluated. The method employed for evaluating cellular binding is dependent on the selected label. For example, in a preferred embodiment, the label is a fluorescent dye and the cellular binding of the labeled ligand is evaluated in a flow cytometer employing conventional techniques. Suitable methods evaluating cellular binding may also include monoclonal antibodies labeled with a fluorescent dye or radiolabeled LDL or monoclonal antibodies. Cellular binding may suitably be evaluated with epifluorescent microscopy or equipment to detect radiolabel employing conventional techniques.

In the second method of the invention blood derived cells from a patient are contacted with a labeled ligand capable of binding LDL receptors and the resulting mixture is incubated under physiological conditions for a period sufficient to allow cellular internalization of the labeled ligand-receptor complex. Suitable and preferred sources of blood derived cells, labeled ligand, and buffers are as specified above. Preferably, the incubation of the cells and ligand is conducted for a period of from about 30 minutes to about 20 hours and, most preferably, for about 2 hours. Suitable temperatures are from about 20° C. to about 40° C. and, preferably, from about 30° C. to about 38° C. Following incubation, cellular internalization of the labeled composition is evaluated. In a preferred embodiment, the internalization of the labeled ligand-receptor composition is evaluated in a flow cytometer employing conventional techniques.

In one embodiment of the above method, the blood derived cells are pretreated by incubation in a cholesterol-free medium to derepress expression of LDL receptors on the blood derived cells. It has been found that individuals with hypercholesterolemia, either heterozygous or homozygous, have little or no ability respectively, for either producing or internalizing LDL receptors in their cells and individuals with pathological diseases such as diabetes and thyroiditis exhibit various defects in lipid metabolism. Also, normal individuals who consume excessive amounts of cholesterol suppress normal LDL receptor production.

It has been found that one method for distinguishing true genetic or pathological conditions from normal individuals is to incubate cells in a cholesterol-free medium. The incubation in cholesterol-free medium allows for new receptors to be synthesized and expressed in the normal individual. It has been found that individuals with genetic defects exhibit little or no ability to express this upregulation of receptors. Any complete cell culture minimal medium is suitable for the derepression incubation. The most preferred medium is RPMI 1640 supplemented with 5% lipid free fetal bovine serum and 10 ug insulin/mL. Preferably, the pretreatment is conducted at a temperature of from about 35° C. to about 40° C. and for a period of from about 18 hours to about 72 hours. The most preferred period for derepression incubation is from about 20 hours to about 24 hours.

The invention also provides a diagnostic agent for use in the first and second methods described above which comprises a ligand capable of binding LDL receptors and a fluorescent label. As stated above, suitable ligands include LDL purified from a biological source and antibodies specific for LDL receptors. Preferably, LDL is purified from whole blood of human, bovine, canine, avian, equine or porcine origin and, most preferably, from human or porcine origin.

In this preferred embodiment, the ligand is labeled using conventional techniques with fluorescent dye. Preferred labels for LDL are selected from the group consisting of DiI (1,1'dioctadecyl-3,3,3',3'-tetramethylindocarbocyanine perchlorate), DiO (3,3'dioctadecyloxacarbocyanine perchlorate), and S-467 (N-[3-sulfopropyl]-4-[p-di-decylaminostyryl]pyridinium). Advantages associated with the specified labels include excitation in a range acheivable by the vast majority of flow cytometers. DiO can be combined with DiI for double label experiments or diagnostic tests (i.e. LDL, HDL receptor assay ratios), DiO has a sharp emission peak that does not overlap with DiI. The advantage of S-467 is the intensity of its emission making quantitative results very sensitive.

Monoclonal antibodies specific for LDL receptors are produced by antibody-producing cell lines which may be hybrid cell lines commonly known as hybridomas. The hybrid cells are formed by the fusion of an anti-LDL receptor antibody-producing cell and an immortalizing cell line. In the formation of the hybrid cell lines, the first fusion partner—the anti-LDL receptor antibody-producing cell—may be a spleen cell of an animal immunized against an LDL receptor positive T cell or a biological preparation comprising LDL receptor. Alternatively, the anti-LDL receptor producing cell may be a B lymphocyte obtained from the spleen, lymph nodes or other tissue. The second fusion partner—the immortal cell—may be a lymphoblastoid cell or a plasmacytoma cell such as a myeloma cell, itself an antibody-producing cell but also malignant.

Murine hybridomas which produce LDL receptor specific monoclonal antibodies are formed by the fusion of mouse myeloma cells and spleen cells from mice immunized against a LDL receptor positive T cells, purified LDL receptor, or other biological preparations comprising LDL receptor. To immunize the mice, a variety of different protocols may be followed. For example, mice may receive primary and boosting immunizations of LDL receptor positive T cells. The fusions are accomplished by standard procedures well known to those skilled in the field of immunology. Kohler and Milstein, *Nature*, 256:495–497 1975) and Kennet, *Monoclonal Antibodies* (Kennet et al., eds. pp.365–367, Plenum Press, N.Y., 1980).

The resulting clones are then screened for production of antibody reactive with LDL receptor positive T cells or biological preparations comprising LDL receptor. Those which secrete reactive antibodies are cloned and the desired monoclonal antibody is purified from said clones using conventional immunological techniques.

The present invention is further described by the following examples wherein all parts and percentages are by weight and degrees are Celsius.

EXAMPLE

A. Procedure for testing functional activity of low density and/or high density lipoprotein receptors in human mononuclear cells I. Isolation of Lipoproteins and Fluorescence Labeling.

Porcine LDL was isolated from whole blood obtained from a local abattoir. 1000 mL of whole blood was combined with 10 mL of EDTA (10%) at the time of collection. The LDL and HDL components of the whole blood were isolated according to procedures described in *Cancer Research*, 43:4600–4605 (1983) and *J. Lipid Research*, 20:217-229 (1979). Whole blood was centrifuges at 5,000×g for 30 minutes at 4° C. to remove the cellular components. The density of the plasma was increased to 1.019 g/mL with KBr. Samples were ultracentrifuged at 300,000×g for 30 hours at 4° C. The lipoprotein layer was removed and the density adjusted to 1.065 g/mL with KBr. Samples were again ultracentrifuged at 300,000×g for 40 hours at 4° C. LDL and HDL bands were removed. The individual components were dialyzed against 0.9% NaCl 0.3 mM EDTA pH 7.4 to remove the KBr. Samples were stored at 4° C.

The resulting purified lipoproteins were fluorescently labeled with DiI, DiO, or S-467 according to the method described in *J. Cell Biology*, 90:595-604 (1981). Two (2) mg of lipoprotein solution were combined with 25 mg of insoluble potato starch, frozen in liquid nitrogen and lyophilized. Lyophilized samples were mixed with 2 mg of the fluorescent dye dissolved in 0.5 mL methanol, and placed at 4° C. for 2 hours. The mixture was evaporated to dryness under nitrogen at 4° C. One mL of buffer, 0.12M NaCl, 10 mM Tricine pH 8.2, was added. The mixture was incubated 41 hours at 4° C. Starch was removed via centrifugation at 4,000×g for 20 minutes at 4° C. The supernatant containing the buffer and suspended labeled lipoproteins was removed and stored at 4° C. protected from light.

II. Patient Blood Collection.

Seven-10 mL samples of whole blood were collected from patients via venipuncture into an ACD solution A Vacutainer TM brand blood collection tubes (yellow top; Becton Dickinson and Co.). Immediately following collection, three (3) 0.5 mL aliquots were placed into 50 mL conical tubes. The aliquots were diluted to a final volume of 50 mL with HBSS without calcium. It has ben found that initial washes with calcium-free medium reduce clotting and helps preserve the lipoprotein receptors. The tubes were centrifuged for 8 minutes at 350×g at 22°-24° C. The resulting wash supernatants were discarded and the pellets are resuspended to a final volume of 50 mL with HBSS without calcium and recentrifuged as described above. The resulting pellets were resuspended in 2 mL HBSS and supplemented with 2 mg/mL BSA and 2 mM $CaCl_2$ at pH 7.4.

III. Incubation of Fluorescent Lipoproteins with Blood Derived Samples.

The three blood samples, described above and designated A, B, and C hereinafter, were maintained at the following temperatures: A and B at 4° C. and C at 37° C. Fifteen (15) ug of the labeled lipoprotein described above were added to B and C, and A was maintained as a control for determining autofluorescence. All three samples are incubated for two hours. The resulting samples were then fixed by the addition of 5 mL of 4% formaldehyde in PBS at 4° C. for five minutes and then for five minutes at ambient temperature. It was discovered that if lysing of RBCs (red blood cells) precedes fixation, the assay does not yield consistent results and that if cells are fixed for a shorter period of time, fixation is inadequate while longer periods of fixation reduce the ability to lyse RBCs.

Lysing of RBCs to completion was accomplished by adding 15 mL of deionized water at 4° C. As soon as RBC lysis is complete, the volume of each sample was brought up to 50 mL with PBS supplemented with 5% BSA to prevent WBC lysis from occurring. The resulting samples were washed twice by centrifugation for eight minutes at 350×g at ambient temperature. (Unbound fluorescent lipoproteins remain in solution and are discarded with the supernatant.) The final pellets were resuspended in 0.5 mL PBS supplemented with 5% BSA. It has been found that the resulting samples are stable at 4° C. for five days if maintained in a light-free environment.

IV. Derepression Assay (LDL Receptor Upregulation)

An additional 1.5 mL of the original 10 mL of the whole blood drawn from the patient were divided into 0.5 mL aliquots and washed as outlined in II. The final pellets were suspended in 30 mL of RPMI 1640 medium supplemented with 5% lipid-free fetal bovine serum and 10 ug/mL insulin. The resulting cells were incubated for 24 hours at 37° C. in the conical tubes with loosened caps. The cells were centrifuged and then washed in HBSS as outlined in II. Fluorescent LDL or HDL binding is performed as outlined in III.

It has been found from studies involving the blood of twenty normal patients that LDL receptors increase up to about 400% following incubation in lipid-free medium for 24 hours. Preliminary data for people with various pathologies indicate that the upregulation effect for the most part, is far less dramatic.

V. Results of Histogram Comparisons.

Relative number of receptors ($S_1$), or binding at 4° C., is expressed as the difference in intensity of fluorescence (channel number) between the unlabeled control and sample labeled at 4° C. Differences are read for 95% of the cell population. Uptake, or ability of receptors to internalize LDL into the cell, ($S_2$), is expressed as the difference in the intensity of fluorescence between the sample labeled at 4° C. and the samples labeled at 37° C. As shown in FIG. 1, the ratio $S_1/S_2$ in normal individuals is approximately 1:3 to 1:4.

The rate of synthesis of new receptors is measured as the ratio between $S_1$ from freshly labeled cells and $S_1$ from the derepressed cells. For normal individuals, the range is approximately 1:4. The relative number of receptors and the uptake of LDL, along with derepression, will yield information reflecting the physiological status, as pertaining to lipoprotein metabolism, in patients tested.

What is claimed is:

1. A method for evaluating lipoprotein receptor function in an individual suspected of having a defect in cholesterol metabolism, comprising the steps of:
   (a) providing a sample of anticoagulated whole blood from the individual;
   (b) washing the sample with a buffered liquid sufficient to release bound lipoproteins from cell-surface receptors, whereby the lipoprotein components of the whole blood sample are removed, including both serum and receptor-bound lipoproteins;
   (c) resuspending the sample in a buffered liquid sufficient to allow the binding of lipoproteins to cell-surface receptors;
   (d) dividing the resuspended sample of (c) into three portions;
   (e) adjusting the temperatures of the portions of the resuspended sample by equilibrating the first and second portions thereof to below physiological temperature and the third portion thereof to physiological temperature;
   (f) adding to the second and third portions of the resuspended sample a suspension of labelled lipoproteins;
   (g) incubating the three portions of the resuspended sample at the temperature to which each has been equilibrated as indicated in (e) and in the presence of labelled lipoproteins as indicated in (f) for a sufficient period of time for lipoproteins to bind to cell-surface receptors and, at physiological temperature, to become internalized within cells;
   (h) following the incubation of (g), exposing the three portions to a fixing agent, whereby cell-surface receptor-bound labelled lipoproteins become cross-linked to lipoprotein receptors and cellular internalization of labelled lipoproteins ceases;
   (i) washing the fixed portions of (h) with an isotonic liquid, sufficiently to separate unbound labelled lipoproteins from cell-associated labelled lipoproteins; and
   (j) detecting the presence of cell-associated labelled lipoproteins.

2. A method of claim 1 wherein the first and second portions of (e) are cooled to below physiological temperature by means of an icewater bath.

3. A method of claim 1 including the additional step of determining the number of lipoprotein receptors per cell by evaluating the difference between the amount of cell-associated labelled lipoproteins in the first portion and the second portion.

4. A method of claim 1 including the additional step of evaluating the ability of the individual's cells to internalize labelled lipoproteins by evaluating the difference between the second portion and the third portion.

5. A method of claim 1 wherein the sample of anticoagulated whole blood obtained from the individual is from at least about 1.5 mL up to about 10 mL in volume.

6. A method of claim 1 wherein the buffered liquid of (b) is an isotonic balanced salts solution formulated to be substantially free of divalent cations.

7. A method f claim 1 wherein the buffered liquid of (b) is a calcium-free formulation of Hank's balanced salts solution.

8. A method of claim 1 wherein the suspension of labelled lipoproteins added in (f) is comprised of LDLs derived from human, porcine, bovine, equine, canine or avian origins which are labelled with a lipophilic fluorescent dye.

9. A method of claim 8 wherein the lipophilic fluorescent dye is selected from the group consisting of:
   i) 1,1'-dioctadecyl-3,3,3',3'-tetramethylindocarbocyanine perchlorate (diI),
   ii) 3,3'-dioctadecyloxacarbocyanine perchlorate (diO), and
   iii) N-(3-sulfopropyl)-4-(p-di-decylaminostyryl)-pyridinium (S-467).

10. A method of claim 8 wherein the suspension of labelled lipoproteins added in (f) is comprised of porcine LDLs labelled with 1,1'-dioctadecyl-3,3,3',3'-tetramethylindocarbocyanine perchlorate (diI).

11. A method of claim 1 wherein the incubation of (g) is from about 30 min up to about 20 hours.

12. A method of claim 11 wherein the incubation of (g) is about 2 hours.

13. A method of claim 1 including the additional step of contacting the fixed portions of (h) with a hypotonic liquid sufficient to lyse red blood cells.

14. A method of claim 1 wherein the suspension of labelled lipoproteins added in (f) is comprised of LDLs labelled with a fluorescent dye and the presence of cell-associated labelled lipoproteins is detected by fluorescence-activated flow cytometry.

15. A method of claim 1 including the additional steps of;
   (1) resuspending the washed sample of (b) in a cell culture medium sufficient to derepress the synthesis of new lipoprotein receptors, the medium comprised of (i) a complete cell culture minimal medium, (ii) insulin, and (iii) lipid-free fetal bovine serum; and
   (2) culturing the suspension of (a) under conditions sufficient to promote cell metabolism for a period of time sufficient for new lipoprotein receptors to be synthesized.

16. A method of claim 15 wherein the suspension of (1) is cultured for about 20 hours to about 24 hours.

17. A method for evaluating lipoprotein metabolism in an individual, comprising the steps of:
   (a) providing a sample of anticoagulated whole blood from the individual;
   (b) washing the sample with a buffered liquid sufficient to release bound lipoproteins from cell-surface receptors, whereby the lipoprotein components of the whole blood sample are removed, including both serum and receptor-bound lipoproteins;
   (c) resuspending a portion of the sample in a buffered liquid sufficient to allow the binding of lipoproteins to cell-surface receptors;
   (d) dividing the resuspended portion of (c) into three subportions, hereinafter {1}-{3};
   (e) evaluating lipoprotein receptor function in subportions {1}, {2} and {3} by
      i) adjusting the temperatures of subportions {1}-{3} of the resuspended sample by equilibrating {1} and {2} to below physiological temperature and {3} to physiological temperature;
      ii) adding to {2} and {3} a suspension of labelled lipoproteins;
      iii) incubating subportions {1}, {2} and {3} at the temperature to which each has been equilibrated as indicated in (i) and in the presence of labelled lipoproteins as indicated in (ii) for a sufficient period of time for lipoproteins to bind to cell-surface receptors and, at physiological temperature, to become internalized within cells;

iv) following the incubation of (iii), exposing subportions {1}, {2} and {3} to a fixing agent, whereby cell-surface receptor-bound labelled lipoproteins become crosslinked to lipoprotein receptors and cellular internalization of labelled lipoproteins ceases;

(v) washing the fixed subportions of (iv) with an isotonic liquid, sufficiently to separate unbound labelled lipoproteins from cell-associated labelled lipoproteins;

(vi) detecting the presence of cell-associated labelled lipoproteins in the washed, fixed subportions {1}, {2} and {3};

(f) resuspending a second portion of the washed sample of (b) in a cell culture medium sufficient to derepress the synthesis of new lipoprotein receptors, where in the medium is comprised of (i) a complete cell culture minimal medium, (ii) insulin, and (iii) lipid-free fetal bovine serum;

(g) culturing the suspension of (f) under conditions sufficient to promote cell metabolism for a period of time sufficient for new lipoprotein receptors to be synthesized;

(h) washing and resuspending the cultured, derepressed, suspension of (g) in a buffered liquid sufficient to allow the binding of lipoproteins to cell-surface receptors;

(i) dividing the derepressed sample of (h) into three subportions, hereinafter {4}-{6}; and (j) evaluating lipoprotein receptor function in the derepresed subportions {4}, {5} and {6} as described in (e) for the fresh subportions {1}, {2} and {3}.

18. A method of claim 17 wherein the subportions {1} and {2} are equilibrated to below physiological temperature by means of an icewater bath.

19. A method of claim 17 including the additional step of determining the number of lipoprotein receptors per cell by evaluating the difference between the amount of cell-associated labelled lipoproteins in subportions {1} and {2}.

20. A method of claim 17 including the additional step of evaluating the ability of the individual's cells to internalize labelled lipoproteins by evaluating the difference between subportions {2} and {3}.

21. A method of claim 17 including the additional step of evaluating the ability of the individual's blood cells to respond to the absence of lipoproteins by derepressing the synthesis of lipoprotein receptors, the additional step comprising evaluating the difference between the number of lipoprotein receptors observed on fresh cells and on cells cultured in the absence of lipoproteins.

22. A method of claim 17 including the additional step of evaluating the ability of the individual's blood cells to respond to the absence of lipoproteins by derepressing the synthesis of lipoprotein receptors, the additional step comprising evaluating the ratio of the subportions ({5}-{4})/({2}-{1}).

23. A method of claim 17 wherein the sample of anticoagulated whole blood obtained from the individual is from at least about 3 mL up to about 10 mL in volume.

24. A method of claim 17 wherein the buffered liquid of (b) is a calcium-free formulation of Hank's balanced salts solution.

25. A method of claim 17 wherein the suspension of labelled lipoproteins added in (f) is comprised of LDLs derived from a source selected from human, porcine, bovine, equine, canine and avian origins which are labelled with a lipophilic fluorescent dye, and the presence of cell-associated labelled lipoproteins is detected by fluorescence-activated flow cytometry.

26. A method of claim 25 wherein the lipophilic fluorescent dye is selected from the group consisting of:
 i) 1,1'-dioctadecyl-3,3,3',3'-tetramethylindocarbocyanine perchlorate (diI),
 ii) 3,3'-dioctadecyloxacarbocyanine perchlorate (diO), and
 iii) N-(3-sulfopropyl)-4-(p-di-decylaminostyryl)-pyridinium (S-467).

27. A method of claim 25 wherein the suspension of labelled lipoproteins added in (f) is comprised of porcine LDLs labelled with 1,1'-dioctadecyl-3,3,3',3'-tetramethylindocarbocyanine perchlorate (diI).

28. A method of claim 17 wherein the incubation of (e) (iii) is about 2 hours.

29. A method of claim 17 including the additional step of contacting the fixed subportions of (h) with a hypotonic liquid sufficient to lyse red blood cells.

30. A method of claim 17 wherein the suspension of (f) is cultured for about 20 hours to about 24 hours.

31. A kit for evaluating lipoprotein receptor function, comprising:
 (a) a calcium-free buffer sufficient to release bound lipoproteins from cell-surface receptors;
 (b) an organic or ionic buffer having a pH of from about 7.2 to about 8.0, containing calcium, said buffer being suitable for the binding of lipoproteins to cell-surface receptors;
 (c) a labelled lipoprotein preparation; and
 (d) a fixing agent sufficient to crosslink cell-surface receptor-bound labelled lipoproteins to lipoprotein receptors and to prevent cellular internalization of labelled lipoproteins.

32. A kit of claim 31 comprising
 (a) a calcium-free formulation of Hank's balanced salts solution;
 (b) a formulation comprising Hank's balanced salts solution, a nonspecific protein, and calcium;
 (c) a preparation of porcine LDLs labelled with 1,1'-dioctadecyl-3,3,3',3'-tetramethyl-indocarbocyanine perchlorate (diI);
 (d) a formaldehyde preparation; and further comprising
 (e) a calibration standard for fluorescence-activated cell sorting analysis, comprising a preparation of calibrated diI-labelled particles.

33. A kit for evaluating lipoprotein metabolism, comprising:
 (a) a calcium-free buffer sufficient to release bound lipoproteins from cell-surface receptors;
 (b) an organic or ionic buffer having a pH of from about 7.2 to about 8.0, containing calcium, said buffer being suitable for the binding of lipoproteins to cell-surface receptors;
 (c) a labelled lipoprotein preparation;
 (d) a fixing agent sufficient to crosslink cell-surface receptor-bound labelled lipoproteins to lipoprotein receptors and to prevent cellular internalization of labelled lipoproteins; and
 (e) a cholesterol-free cell culture medium sufficient to derepress the synthesis and expression of new lipoprotein receptors in a normal individual.

34. A kit of claim 33 comprising
(a) a calcium-free formulation of Hank's balanced salts solution;
(b) a formulation comprising Hank's balanced salts solution, a nonspecific protein, and calcium;
(c) a preparation of porcine LDLs labelled with 1,1'-dioctadecyl-3,3,3',3'-tetramethyl-indocarbocyanine perchlorate (diI);
(d) a formaldehyde preparation; and
(e) a derepression medium comprised of a complete cell culture minimal medium formulation, insulin, and lipid-free fetal bovine serum; and further comprising
(f) a calibration standard for fluorescence-activated cell sorting analysis, comprising a preparation of calibrated diI-labelled particles.

* * * * *

UNITED STATES PATENT AND TRADEMARK OFFICE
CERTIFICATE OF CORRECTION

PATENT NO. : 5,135,848
DATED : August 4, 1992
INVENTOR(S) : John H. Abel, Barbara Obrepalska-Bielska and Kathy Gottlund It is certified that error appears in the above-identified patent and that said Letters Patent is hereby corrected as shown below:

Cover Page, under Inventors, delete "Allentown, both of Pa" and insert therefor --Allentown; Kathy Gottlund, Kutztown, all of Pa.--

Column 7, Claim 7, Line 64, cancel "f" and insert therefor --of-- and change "claim 1"--claim 6 --.

Signed and Sealed this

Twenty-eighth Day of December, 1993

Attest:

BRUCE LEHMAN

Attesting Officer         Commissioner of Patents and Trademarks